(12) United States Patent
Björklund et al.

(10) Patent No.: US 6,325,786 B1
(45) Date of Patent: Dec. 4, 2001

(54) ABSORBENT ARTICLE HAVING INCREASED FRONT PORTION STIFFNESS

(75) Inventors: Camilla Björklund, Mölnlycke; Urban Widlund, Pixbo; Ann Samuelsson, Lindome; Solgun Drevik, Mölnlycke; Anders Gustafsson, Billdal, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/297,584

(22) PCT Filed: Nov. 11, 1997

(86) PCT No.: PCT/SE97/01882

§ 371 Date: Aug. 12, 1999

§ 102(e) Date: Aug. 12, 1999

(87) PCT Pub. No.: WO98/22058

PCT Pub. Date: May 28, 1998

(30) Foreign Application Priority Data

Nov. 15, 1996 (SE) .................................................... 9604222

(51) Int. Cl.⁷ ............................. A61F 13/15; A61F 13/20
(52) U.S. Cl. ................... 604/385.01; 604/358; 604/378; 604/367
(58) Field of Search .............................. 604/358, 385.01, 604/385.04, 385.03, 385.21, 385.23, 397

(56) References Cited

U.S. PATENT DOCUMENTS

| | | |
|---|---|---|
| H1634 | 2/1997 | Oetjen et al. . |
| 810,119 | 1/1906 | Green . |
| 810,120 | 1/1906 | Green . |
| 810,131 | 1/1906 | Green . |
| 1,946,626 * | 2/1934 | Jurgensen .......................... 604/385.1 |
| 2,551,663 | 5/1951 | Fox . |
| 3,407,814 | 10/1968 | George et al. . |
| 3,468,311 | 9/1969 | Gallagher . |
| 3,570,493 | 3/1971 | Olsson . |
| 3,888,255 | 6/1975 | Shah et al. . |

(List continued on next page.)

FOREIGN PATENT DOCUMENTS

| | | |
|---|---|---|
| 0 067 377 | 12/1982 | (EP) . |
| 0 155 515 A1 | 9/1985 | (EP) . |
| 0 155 515 B1 | 9/1985 | (EP) . |

(List continued on next page.)

OTHER PUBLICATIONS

U.S. application No. 09/297,366, Johansson et al., filed Jul. 7, 1999, (WO 98/22060).
U.S. application No. 09/297,583, Gustafsson et al., filed Aug. 3, 1999, (WO 98/22059).

(List continued on next page.)

Primary Examiner—John G. Weiss
Assistant Examiner—Michele Kidwell
(74) Attorney, Agent, or Firm—Burns, Doane, Swecker & Mathis, L.L.P.

(57) ABSTRACT

The invention relates to an absorbent article such as a sanitary napkin, an incontinence guard or a panty-liner, which article has a generally elongated shape with a longitudinal direction and a transverse direction and exhibits two long sides, two short sides, two end portions and a central portion, located between the end portions, and exhibiting a transversely extending cross-sectional line from which the width of the article increases in a direction towards a short side of the article, whereby the end portion located at the short side exhibits a maximum width which is larger than the width of the central portion, whereby the article changes inclination at the cross-sectional line, whereby the inclination is defined by an angle between the long side of the article and a longitudinal line parallel to the longitudinal direction of the article, which article exhibits a width of the central portion which has an upper limit of 60 mm, and an angle of 30–90°, and the article has a stiffness, at least in the front portion, which exceeds 100 N measured according to ASTM D 4032-82.

13 Claims, 4 Drawing Sheets

U.S. PATENT DOCUMENTS

| | | |
|---|---|---|
| 4,041,950 | 8/1977 | Jones, Jr. . |
| 4,047,531 | 9/1977 | Karami . |
| 4,195,634 | 4/1980 | DiSalvo et al. . |
| 4,217,901 | 8/1980 | Bradstreet et al. . |
| 4,351,340 | 9/1982 | McLeod . |
| 4,386,932 | 6/1983 | Pitts . |
| 4,536,181 | 8/1985 | Cook . |
| 4,643,726 | 2/1987 | Gegelys . |
| 4,673,403 | 6/1987 | Lassen et al. . |
| 4,804,380 | 2/1989 | Lassen et al. . |
| 4,828,555 * | 5/1989 | Hermansson ............ 606/379 |
| 4,846,824 | 7/1989 | Lassen et al. . |
| 4,865,597 | 9/1989 | Mason, Jr. et al. . |
| 4,897,084 | 1/1990 | Ternström et al. . |
| 4,911,701 | 3/1990 | Mavinkurve . |
| 5,032,121 | 7/1991 | Mokry . |
| 5,074,855 | 12/1991 | Rosenbluth et al. . |
| 5,074,856 | 12/1991 | Coe et al. . |
| 5,080,658 | 1/1992 | Igaue et al. . |
| 5,098,422 * | 3/1992 | Davis et al. ............ 604/385.1 |
| 5,114,419 | 5/1992 | Daniel et al. . |
| 5,129,893 | 7/1992 | Thorén . |
| 5,171,302 * | 12/1992 | Buell ..................... 604/385.1 |
| 5,181,563 | 1/1993 | Amaral . |
| 5,197,959 | 3/1993 | Buell . |
| 5,295,987 | 3/1994 | Widlund et al. . |
| 5,354,400 | 10/1994 | Lavash et al. . |
| 5,374,260 * | 12/1994 | Lemay et al. ............ 604/378 |
| 5,383,868 | 1/1995 | Hyun . |
| 5,454,802 | 10/1995 | Lindquist et al. . |
| 5,460,623 | 10/1995 | Emenaker et al. . |
| 5,545,156 | 8/1996 | DiPalma et al. . |
| 5,558,656 | 9/1996 | Bergman . |
| 5,569,231 | 10/1996 | Emenaker et al. . |
| 5,591,150 | 1/1997 | Olsen et al. . |
| 5,624,421 | 4/1997 | Dabi et al. . |
| 5,688,259 | 11/1997 | Osborn, III et al. . |
| 5,695,324 | 12/1997 | Weirich . |
| 5,704,931 | 1/1998 | Holtman et al. . |
| 5,722,967 | 3/1998 | Coles . |
| 5,741,241 | 4/1998 | Guidotti et al. . |
| 5,827,258 | 10/1998 | McFall et al. . |
| 5,849,003 | 12/1998 | Olsen et al. . |
| 5,873,869 | 2/1999 | Hammons et al. . |
| 5,919,178 | 7/1999 | Widlund . |
| 5,957,909 | 9/1999 | Hammons et al. . |
| 5,961,508 | 10/1999 | Mayer et al. . |
| 6,020,536 | 2/2000 | Osterdahl et al. . |
| 6,033,391 | 3/2000 | Osborne, III et al. . |
| 6,042,575 | 3/2000 | Osborn, III et al. . |
| 6,080,909 | 6/2000 | Osterdahl et al. . |

FOREIGN PATENT DOCUMENTS

| | | |
|---|---|---|
| 0 235 763 | 9/1987 | (EP) . |
| 0 248 173 | 12/1987 | (EP) . |
| 0 335 252 A2 | 10/1989 | (EP) . |
| 0 335 253 A1 | 10/1989 | (EP) . |
| 0 335 253 B1 | 10/1989 | (EP) . |
| 0 336 578 | 10/1989 | (EP) . |
| 0 339 041 B1 | 11/1991 | (EP) . |
| 0 606 082 A1 | 7/1994 | (EP) . |
| 0 419 434 B2 | 11/1998 | (EP) . |
| 2 694 187 | 2/1994 | (FR) . |
| 2 119 656 | 11/1983 | (GB) . |
| 2 119 657 | 11/1983 | (GB) . |
| 92/19197 | 11/1992 | (WO) . |
| 93/15702 | 8/1993 | (WO) . |
| 93/21879 | 11/1993 | (WO) . |
| 95/31165 | 11/1995 | (WO) . |
| 96/20679 | 7/1996 | (WO) . |
| 96/26699 | 9/1996 | (WO) . |
| 97/09015 | 3/1997 | (WO) . |
| 98/22058 | 5/1998 | (WO) . |

OTHER PUBLICATIONS

U.S. application No. 09/297,365, Björklund et al., filed Aug. 2, 1999, (WO 98/22057).

U.S. application No. 09/297,637, Björklund et al., filed Aug. 4, 1999, (WO 98/22061).

U.S. application No. 09/297,746, Samuelsson et al., filed Sep. 1, 1999, (WO 98/22062).

* cited by examiner

ABSORBENT ARTICLE HAVING INCREASED FRONT PORTION STIFFNESS

TECHNICAL FIELD

Absorbent article, such as a sanitary napkin, an incontinence guard or a panty-liner, which article has a substantially elongated shape with a longitudinal direction and a transverse direction and exhibits two long sides, two short sides, two end portions and a central portion located between the end portions, which central portion exhibits a transversely extending cross-sectional line from which the width of the article increases in a direction towards a short side of the article, wherein the end portion located at the short side exhibits a maximum width which is larger than the width of the central portion, wherein the long sides of the article change inclination at the cross-sectional line, wherein the inclination is defined by an angle a between the long side of the article and a longitudinal line parallel to the longitudinal direction of the article.

BACKGROUND OF THE INVENTION

Conventional absorbent articles of the above-mentioned kind exhibit a substantially rectangular shape. A problem associated with this design is that the articles are not adapted to the body of the user. As a rule, they are too wide in the central portion of the article, that is to say the portion of the article which is intended to fit in between the thighs of the user. Consequently, the article will wrinkle during use. This is both uncomfortable for the user and increases the risk of leakage. In order to solve this problem it has been suggested to make the absorbent articles hourglass-shaped rather than rectangular. Such articles are previously known from, for instance, EP 67 377 and EP 235 763.

Normally, absorbent articles of the above-mentioned kind are attached in the crotch portion of the underwear of the user by means of adhesive areas applied to the article.

A problem with this type of attachment is that the adhesive areas may be contaminated so that they lose their attachment capability. Another problem with adhesive attachment is that adhesive may adhere permanently to the underwear of the user, that is to say the adhesive cannot be washed away and the underwear is ruined. A further problem with adhesive attachment is that protective strips are required in order to protect the adhesive areas. Such protective strips must be removed and discarded before use. Many users of absorbent articles experience this as time-consuming and cumbersome.

A further problem, which is especially obvious if large areas of the article are covered with adhesive, is that the article is more likely to follow the movements of the underwear than of the body. This results in an increased risk of leakage since gaps easily arise between the article and the body of the user. In those cases where the article instead follows the movements of the body, this will lead to the attachment against the underwear being subjected to shear forces. This may imply that the article is detached from the underwear or is deformed. At worst, both these situations may occur simultaneously. The consequence will in all cases be that the article does not cover the areas it is intended for, with leakage as a result.

One way of reducing this problem is by designing the adhesive areas in different ways, as is disclosed in for example GB 2 119 656 and GB 2 119 657, or by combining adhesive areas with areas with high friction, as is disclosed in U.S. Pat. No. 3,888,255.

PURPOSE OF THE INVENTION

The purpose of the invention is to remedy the above-mentioned problems and to provide an article which has a good fit and can stay in place against the body without any aid from special attachment devices.

BRIEF SUMMARY OF THE INVENTION

According to the invention, an article of the kind mentioned in the introduction, in which the problems associated with previously known such articles essentially have been eliminated, is characterized in that the width of the crotch portion is no larger than 60 mm and that the angle $\alpha$ is 30–90°.

Further embodiments are evident from the appended claims.

SUMMARY OF THE INVENTION

By means of the present invention, the problems with poor fit and attachment are solved. This is achieved by designing the article so that its central portion exhibits a smaller width than at least one of its end portions, and by ensuring that the angle between the longitudinal direction of the article and the main direction of the long sides of the article, where the article tapers towards the central portion, is 30–90°. When an article designed in this way is placed with the end portion exhibiting the widest cross-section forwards on the user, that is to say in the groin region of the user, the article will be kept in position in a natural way and no further attachment members such as adhesive surfaces will be required. This is due to the fact that the width of the central portion of the article, and the angle with which this is transformed into the width of the end portion, have been selected in such a way that the article conforms to the anatomy of the user. An article designed in this way is held in the groin of the user and prevents the article from being displaced backwards between the legs of the user. This is a common problem where conventional articles are concerned, since the leg movements of the user feed the article backwards. The angle between the longitudinal direction of the article and the main direction of the long sides of the article, where the article tapers towards the central portion, should be 30–90°. At angles exceeding 90°, the edges of the end portion may come to chafe against the groin area and the legs of the user and thereby create discomfort to the user. The smaller the angle is, the larger is the risk that the article will slide backwards in between the legs of he user. With an angle which is less than 30°, this risk is larger than acceptable. An angle between 35° and 55° provides the best balance between fastening and comfort. An angle of 45° has been found to be particularly favourable.

An alternative way of describing the angle, which is relevant to the invention, is in terms of proportions between the width of the central portion at its narrowest part, and the width of the end portion at its widest part.

The width of the end portion which during use is intended to be facing forwards on the user should be 1.5–5 times as wide at its widest part, as the width of the central portion at the narrowest part.

However, there is also a risk, although not as great, that the article will slide forwards between the legs of the user. This risk is eliminated if the end portion which is intended to be placed backwards on the user is also designed so that its width is larger than the width of the central portion.

It is important that the cross-section or width of the central portion is adapted to the anatomy of the user, so that the article does not wrinkle or crease in the central portion and thereby cause discomfort to the user and possible leakage. From a comfort point of view, where the width of the article is concerned, the most critical region in the crotch portion of the user is where the muscle group passes which has its origin on the inside of the base of the pelvis and its attachment along the thigh. This muscle group consists of the muscles Adductor Brevis, Adductor Longus, Gra0cilis and Adductor Magnus.

Measurements have shown that the distance in the crotch region of the user, between the Adductor muscle groups on the left and the right hand side, is surprisingly similar for all human beings and is between 30 mm and 35 mm.

Fatness, of course, affects the width between the thighs, but the width between the muscle groups in the crotch region is the same and these are the ones which give rise to the perception that an article is chafing. The fatty tissue is deposited on the outside of the muscles, but does not contribute to the possible feeling of discomfort. If the article is constructed of a very stiff material, the width of the central portion, at least in the area which is intended to fit between the tendons, should not exceed approx. 40 mm and should preferably not exceed approx. 35 mm. This critical area is approx. 5–15 mm long in the longitudinal direction of the article. A very stiff material does not yield or wrinkle but may, on the contrary, chafe against the muscle origin of the user and cause discomfort.

An article composed of a material which is very rigid, and which exhibits a completely straight cross-section, has to have a total width which is smaller than what is necessary when the construction is more flexible. One way of manufacturing a more flexible article is to give its cross-section a shape other than straight. Such a more flexible cross-section may, for example, exhibit one or several ridges. For instance, it may exhibit the basic shape of the letter M.

The rigidity of the article is important in order to avoid the article becoming twisted, bent, cracked or sheared during use. In order to prevent the article losing rigidity when the cross-section of the central portion is made narrower, the edges of the article may be folded or rolled in, at least at the central portion. This makes it possible to use a piece of material, having a total straight cross-section which is too wide to be comfortable. In this way the rigidity of the article is increased, while the comfort is retained.

In order to balance comfort with the required rigidity of the article, it is also possible to use several materials with different stiffness in order to build a central portion with a variable stiffness in the transverse direction. For instance, the central portion may be composed of a centre part of stiffer material with outer parts of a less stiff material. Accordingly, the outer parts will be in contact against the thighs of the user. Consequently, in the longitudinal direction of the article, the outer parts are delimited by the two end portions and, in the transverse direction of the article, by the long sides of the article and the centre part of the central portion situated between the two outer parts. With such a design, the central portion may be allowed to be wider that if merely the stiffer material is used. By reinforcing the centre part of the central portion, the article obtains better stiffness properties than if a less rigid material had been used. At the same time, high comfort for the user may be achieved.

Examples of stiffer materials, which are suitable for use in the centre part of the central portion, are relatively thick layers of polypropylene film, polyethylene film and bonded fibre networks. In this context, a relatively thick material layer refers to material layers with a layer thickness exceeding approx. 0.2 mm. Furthermore, it is possible to enhance the stiffness of a plastic layer by blending the plastic with talc, clay, or other stiffness-increasing fillers. Furthermore, the stiffness of the centre part of the central portion may be obtained by means of stiff inserts of metal or wood, such as plates, rods, skeleton-like constructions or the like. The less stiff outer parts advantageously consist of one or several layers of soft, deformable material such as plastic films and nonwoven layers of the sort which usually are used as cover materials on absorbent articles. The outer parts may further comprise absorbent material, such as absorbent nonwoven sheets, cellulose fluff pulp layers, tissue sheets, or the like.

Preferably, an absorbent article according to the invention has a comparatively small width. However, depending on the materials used, and the design of the central portion of the article, it has been found that the width of the central portion may be varied between 15 mm and 60 mm, preferably between 20 mm and 35 mm. A central portion with a larger width should suitably be compressible by the forces which arise during normal use, so that the width of the central portion during use does not exceed approx. 40 mm, and preferably does not exceed approx. 35 mm.

Furthermore, it has been found that articles which have a width during use which is smaller than approx. 15 mm function poorly with respect to leakage. Therefore, it is suitable if the central portion is at least so stiff, or has such a construction in other respects, that the central portion during use cannot be compressed to a width less than approx. 15 mm.

The entire central portion does not have to fulfill the specified width criteria. As mentioned above, the critical area is constituted by the region of the article which should fit between where the Adductor muscle groups of the left and right side, originating from the inside of the base of the pelvis and having their attachments along the thigh, pass the crotch region of the user. The groin starts is right in front of these. This area corresponds to the region on the article where the article starts to widen and the central portion merges into one of the end portions. As earlier mentioned, the area on the article, which is to fit between the Adductor muscle groups of the thighs, is approx. 5–15 mm long.

As mentioned earlier, the suitable width of the central portion of the article, at least in the above-described critical area, depends on the choice of material and the choice of design for the central portion of the article. If a design with a stiffer material in the centre part and less stiff material in the outer parts is chosen, a suitable width of the stiffer material is approx. 20 mm, and a suitable total width of the central portion is at a 30 maximum approx. 40 mm, and preferably approx. 35 mm. That is to say, each outer part is between approx. 7.5 mm and 1 0mm wide. If the material which is used for the outer parts has the ability to function as a bellows, i. e. to pleat in a controlled way, the central portion may be allowed to be up to approx. 60 mm wide. During use, the pressure from the thighs of the user will compress the article to a width of approx. 30–35 mm in the region in question. Naturally, for all widths larger than approx. 30–35 mm it is true that the central portion of the article will be compressed transversely, provided that the entire central portion is not constituted by a very stiff material. Such a design of very stiff material would instead cut into the thighs of the user and cause discomfort to the user.

Due to the fact that the article is designed so that at least one of its end portions is considerably wider than its central portion, and with the side edges of the article at the wider end portion angled in relation to the side edges at the central portion, the article conforms well to the curvature around the thighs of the user. Thereby, it is particularly suitable that the end portion which during use is intended to be facing forwards on the user exhibits the specified widening in relation to the central portion. Furthermore, the adaptation of the width of the article to the critical area between the muscle groups travelling down on both sides of the crotch is decisive for the fit of the article. Thanks to its shape, an article according to the invention has the ability to stay in place against the body of the user during use without requiring the utilization of special attachment members.

In order to further ensure that the article is kept well in place against the body during use and to prevent the article from sliding in the longitudinal direction, it has been found to be suitable that the widened end portion exhibits fairly high stiffness. The end portion is thus prevented from becoming wrinkled during use, or deformed in another way, so that the article can slide between the thighs of the user. A stiff end portion serves as a kind of hook, which rests against the thighs, and counteracts displacement of the article in the longitudinal direction. It is particularly advantageous if the end portion which during use is intended to be facing forwards on the user is comparatively stiff. A stiff front portion counteracts backwards feeding of the article during use, something which otherwise may be a problem, for example when the user is walking or running.

A further method of improving the fit, and preventing that the article during use is displaced out of position in relation the body of the user, is by curving the article longitudinally in accordance with the curvature on the body of the user. Accordingly, it has been found to be particularly advantageous if the front portion, i. e. the end portion of the article which during use is intended to be facing forwards on the user, is angled upwards in relation to the central portion on the side of the article which is intended to be facing the user.

By means of the front portion of the article being angled upwards from the central portion, so that the front portion in the longitudinal direction of the article conforms better to the shape of the private parts of the user, the risk of the article sliding backwards on the user during use is further reduced. During use, the angled front portion is applied over the private parts of the user and functions as a stopping plate which counteracts that the article is fed backwards by the leg movements of the user. In order to obtain the desired braking effect, it is necessary that the front portion and the crotch portion of the article are so stiff, that the angle between them is essentially maintained even during use. However, for reasons of comfort it may be convenient that edge portions closest to the long sides and the front edge of the article, respectively, are constituted by a less stiff material.

The stiffness which is of importance for maintaining an angle $\beta$ between the front portion and the central portion is primarily the bending resistance towards bending along transversely extending bending lines. The exact value of the angle $\beta$ is of minor significance to the achievement of the desired braking effect, as long as $\beta$ is between 20° and 50°.

The materials which may be utilized in order to enhance the stiffness of the end portions of the article are suitably of the same kind as the stiff materials which have been discussed in connection with the description of a rigid central portion. In order to achieve sufficient stiffness in the finished design it has been found that the intrinsic stiffness, of at least some component in the region of the article in question, should exceed 100 N, measured according to ASTM D 4032-82 "Circular Bend Procedure", which method is described in detail in EP 0 336 578. Thereby, intrinsic stiffness refers to the stiffness of a planar material layer.

BRIEF DESCRIPTION OF THE DRAWINGS

In the following, the invention will be described in greater detail with reference to the embodiments which are shown in the drawings. Thereby.

DETAILED DESCRIPTION OF DRAWINGS AND EMBODIMENTS

Figure 1:
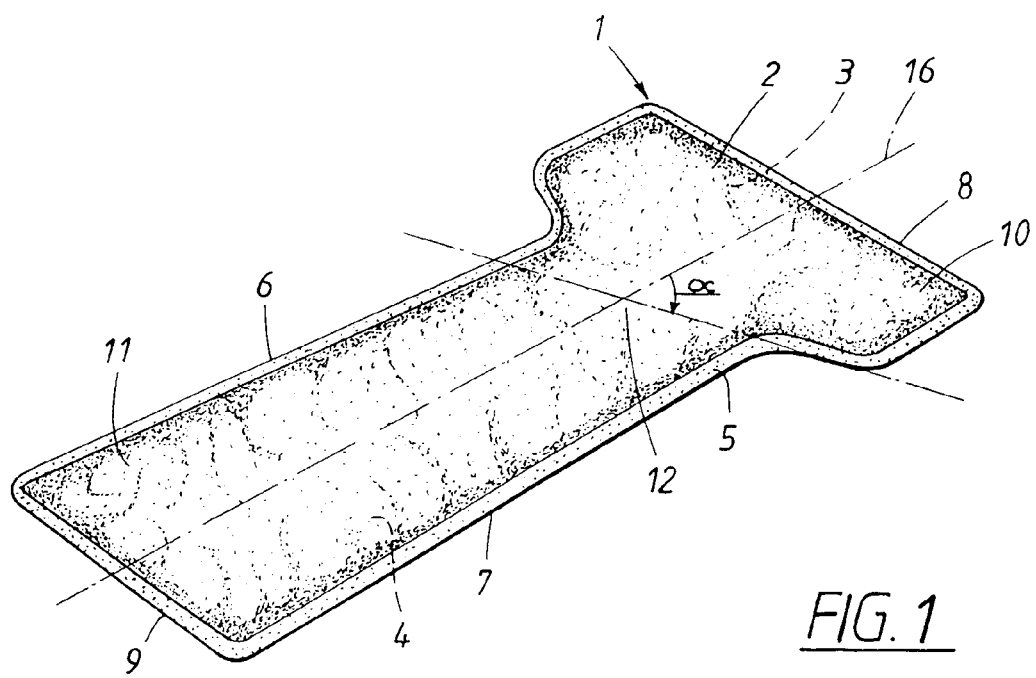
FIG. 1 shows a perspective view of a sanitary napkin according to the invention.
Figure 2:
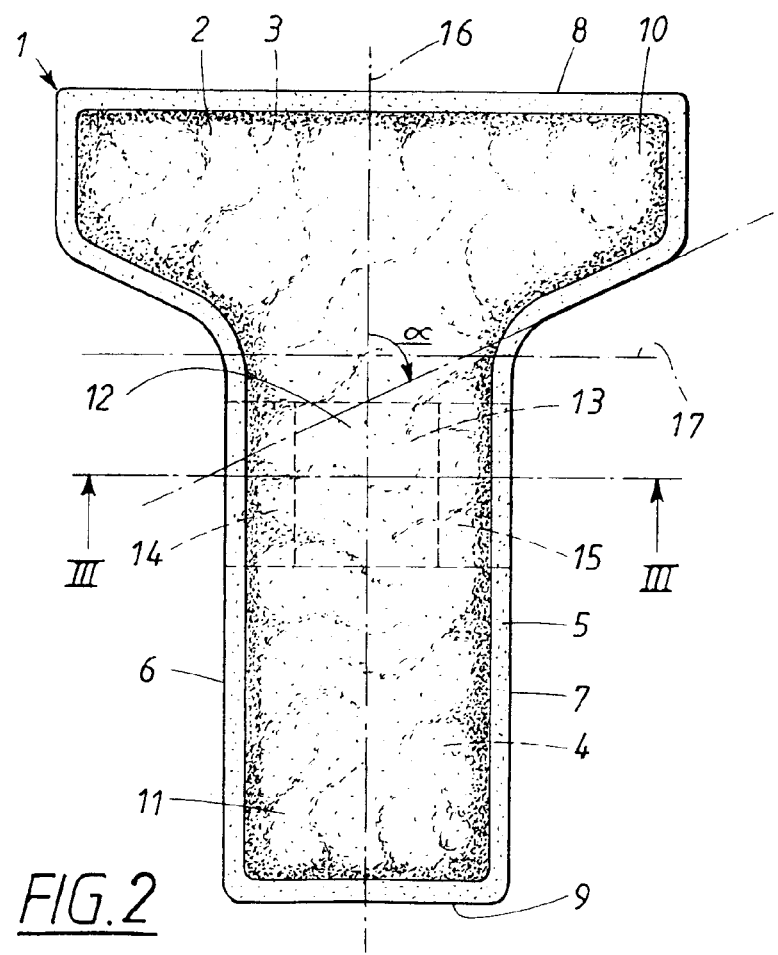
FIG. 2 shows a sanitary napkin according to the invention, seen from the side of the sanitary napkin which is intended to be facing the user.
Figure 3:
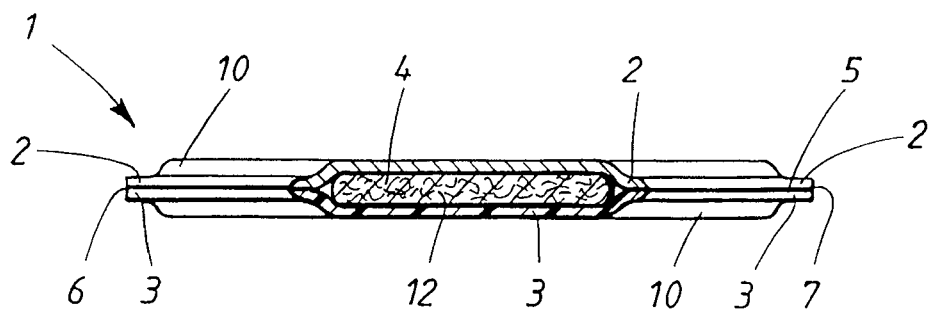
FIG. 3 shows a section along the line III—III through the sanitary napkin in FIG. 2.

The sanitary napkin 1, shown in FIGS. 1, 2 and 3, comprises a liquid-pervious surface layer 2 arranged at the side of the sanitary napkin 1 which during use is intended to be facing the user, a liquid barrier layer 3 arranged on the side of the sanitary napkin 1 which during use is intended to be facing away from the user, and also an absorbent layer 4 arranged between these two layers.

The material in the surface layer 2 may, for example, be a perforated plastic film, a net of plastic or a textile material, a nonwoven or a laminate of, for example, a perforated plastic sheet and a nonwoven sheet. The plastic may be a thermoplastic, such as polyethylene. The nonwoven material may be of natural fibres, such as cellulose or cotton, or synthetic fibres, such as polyethylene, polypropylene, polyester, polyurethane, nylon or regenerated cellulose.

The main tasks of the surface layer 2 in the sanitary napkin, are to conduct the liquid in to the absorbent layer 4, to be soft and pleasant against the body of the user, and to prevent so-called rewetting, i. e. absorbed body fluid penetrating back towards the skin of the user. For reasons of comfort, and in order to avoid skin irritation, it is important that the surface on the portion of the sanitary napkin contacting the skin of the user is maintained as dry as possible during use. Furthermore, a dry surface on the sanitary napkin is perceived as cooler and more pleasant during use, and is more appealing that a soiled, wet surface both purely visually and during handling when changing the sanitary napkin.

The liquid barrier layer, or the backing layer 3 consists of a liquid-impermeable material. Thin, liquid-impervious plastic films are suitable for the purpose, but it is also possible to use materials which originally are liquid-pervious but which have been provided with a coating of plastic, resin, or other liquid-impervious material. In this manner, leakage of liquid from the underside of the absorbent article is prevented. Accordingly, the barrier layer 3 may consist of any material which fulfills the criterion of liquid-impermeability and exhibits sufficient flexibility and skin-friendliness for the purpose. Examples of materials which are suitable as barrier layers are plastic films, nonwoven and laminates of these. Useful plastic films may for example be of polyethylene, polypropylene or polyester. Alternatively, the barrier layer may consist of a laminate of a liquid-impervious plastic layer facing the absorbent body, and a nonwoven facing the underwear of the user. Such a construction results in a leakage-proof barrier layer with a textile feel.

The absorbent layer 4 is suitably manufactured from cellulose fluff pulp. This may be present in the form of reels, bales or sheets which are dry shredded and are transformed into a pulp mat in a fluffed state, sometimes with the admixture of so-called super-absorbents, which are polymers with the ability to absorb several times their own weight of water or body fluid. Examples of other useful materials are different types of natural fibres such as cotton fibres, peat, or the like. It is, of course, also possible to utilize absorbent synthetic fibres, or mixtures of natural fibres and synthetic fibres. Furthermore, the absorbent material may include additional components, such as shape-stabilizing members, liquid-distributing members, or binders such as, for example, thermoplastic fibres which have been heat-treated in order to keep short fibres and particles together as a coherent unit. It is also possible to utilize different types of absorbent foam materials in the absorbent layer.

The two outer layers 2, 3 are mutually interconnected, outside the absorbent layer 4 in a joint 5, located along the periphery of the sanitary napkin.

The sanitary napkin I has a generally elongated shape with a longitudinal direction and a transverse direction and exhibits two long sides 6, 7, two short sides 8, 9, two end portions 10, 11 and a central portion 12, located between the end portions. The central portion exhibits a centre part 13 and two outer parts 14, 15 seen in the transverse direction of the article. In the longitudinal direction of the article, the outer parts are delimited by the two end portions 10, 11, and in the transverse direction of the article, by the long sides 6, 7 of the article and the centre part 13 of the central portion 12, situated between the two outer portions 14, 15.

The central portion 12 exhibits a smaller width than the end portion 10 which is intended to be placed forwards on the user. Thereby, the wider end portion 10 may be held on the front of the thighs of the user and thus prevent that the sanitary napkin from sliding backwards on the user during use.

The widening of the article, in a direction from the central portion 12 towards the wider end portion 10, starts at a transverse cross-sectional line 17. The angle α, which is created between a line parallel to the longitudinal direction of the article and the main direction of the long sides of the article 6, 7 at the wider end portion 10, is between 30° and 90°. As mentioned above, the widening of the end portion 10, and the angle between the side edges 6, 7 of the end portion 10 and the longitudinal direction of the sanitary napkin, are important parameters in order to make the sanitary napkin stay in place during use and not slide backwards between the legs of the user.

The length of the entire article is approx. 150–250 mm. A common length of a sanitary napkin is approx. 200 mm. Out of this total length the central portion 12 and the two end portions 10, 11 may be said to constitute roughly ⅓ each.

Accordingly, a total article length of 150 mm results in a length of 50 mm each for the central portion and the end portions 10, 11. The total length 200 mm results in a length of approx. 70 mm for each portion, and a total length of 250 mm results in a length of approx. 80 mm for each portion. The length ratios between the central portion 12 and the end portions 10, 11, and between the two end portions, may of course deviate from the above specified ⅓ and, accordingly, constitute a larger or smaller portion than ⅓ of the total length of the article. It is common that the back end portion 11 constitutes a larger portion than ⅓ of the total length of the article. The central portion 12 is delimited by the fact that the article is widened from the narrowest spot on the central portion 12 towards the end portion 10 which is intended to be facing forwards on the user. The end portion 10 starts where the article starts to widen.

As specified above, the width of the central portion 12 is 10–45 mm in the narrowest part of the central portion. The width of the widest part of the end portion 10, which is intended to be facing forwards on the user, is 50–200 mm. The ratio between the width and the length of the end portion is important for the stability of the end portion and for the keeping of the article in place against the body. Herein, the length of the central portion refers to the distance from where the article starts to widen from its narrowest spot to the front short end 8 of the article, measured along a centre line 16 through the article which is parallel to the long sides 6, 7 of the article. The length of the end portion is measured along one of the long sides 6, 7 of the article. If the width of the end portion is 100 mm, a suitable length is 50 mm, that is to say a ratio 2:1 between width and length. Analogous to this, a width of 50 mm results in a length of 25 mm, and a width of 200 mm in a length of 100 mm. Deviations from this 2:1 ratio, between width and length of the end portion 10, are of course possible, for instance 3:2–3:1.

In FIG. 3, a cross-section of the sanitary napkin 1 is shown, seen from the end portion 11 which during use is intended to be facing backwards on the user. Herein, a section through the central portion 12 is shown, so that the surface layer 2, the barrier layer 3 and the absorbent layer 4 are seen in cross-section. The end portion 10, which is intended to be facing forwards on the user, can be seen in the drawing with the absorbent layer covered by the surface layer 2 and the barrier layer 3.

Figure 4:
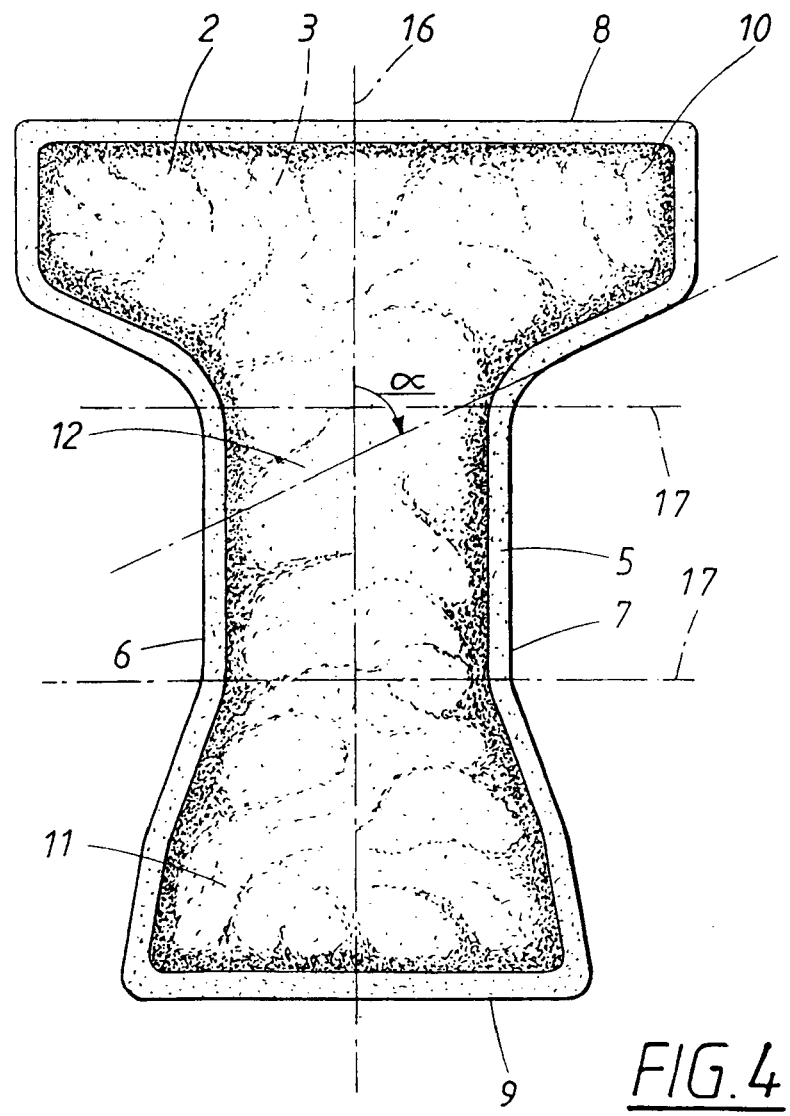
FIG. 4 shows a sanitary napkin according to a second embodiment of the invention, seen from the side of the sanitary napkin which is intended to be facing the user.

In order to eliminate the risk of the article sliding forwards between the legs of the user, the end portion 11 which is intended to be facing backwards on the user may also be designed so that its width is larger than the width of the central portion 12. An article designed in this way is shown in FIG. 4. The widening of the two end portions takes place in a direction from the central portion 12 towards the respective short sides 8, 9 of the article. Thereby, the long sides 6, 7 of the article change inclination at two cross-sectional lines 17, located at both sides of the central portion 12 in the longitudinal direction of the article.

Figure 5:
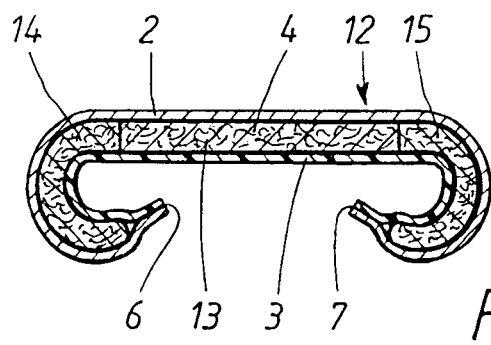
FIG. 5 shows a cross-section through the central portion of a sanitary napkin according to a third embodiment of the invention.

In FIG. 5, an alternative embodiment of the invention is shown, where the absorbent layer 4 is built up from a stiffer material in the centre part 13 of the central portion 12, and a less stiff material in the outer parts 14, 15 of the central portion 12. Such a construction enables the width of the central portion 12 to be larger than if the stiffer material had been selected for the entire absorbent layer 4, with maintained comfort for the user. On the sanitary napkin shown in FIG. 5, the long sides 6, 7 have been folded or rolled in towards its back. This is a measure which lends the sanitary napkin an increased stiffness without the need to use a stiffer material. That is to say, the sanitary napkin obtains increased stiffness and, consequently, an increased resistance to twisting, bending, cracking and shearing, with maintained comfort for the user.

The two designs, shown in FIG. 5, which provide a possibility to balance the required stiffness of the sanitary napkin against user comfort, by selecting different materials in outer and central parts, and by means of using rolled in side edges, may of course also be used separately.

Figure 6:
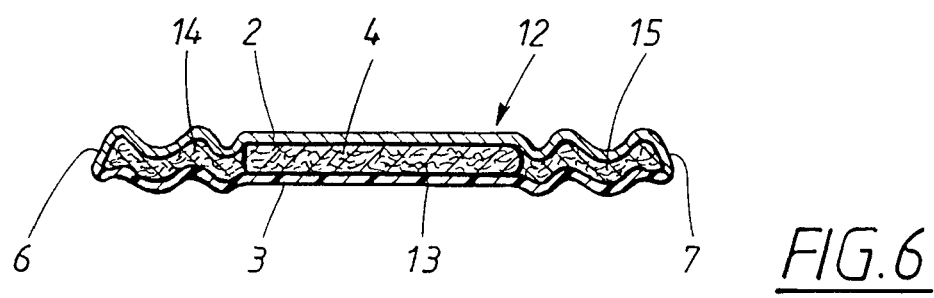
FIG. 6 shows a cross-section through the central portion of a sanitary napkin according to a fourth embodiment of the invention.

In FIG. 6, a cross-section through the central portion 12 of the sanitary napkin is shown after the sanitary napkin has been used. The absorbent layer 4 has been built up from different materials in the centre part 13 and the outer parts 14, 15. The material in the centre part 13 may be a very rigid material, if the outer parts 14, 15 are composed of a material which has the ability to function as a bellows. An article designed in this way, the width of which exceeds the critical distance between the two muscle groups in the crotch of the user, will during compression between the thighs of the user be pleated in the outer parts 14, 15 of the central portion 12, while the centre part 13 retains its planar shape.

In contrast to what is the case with a conventional design, where the entire central portion wrinkles in an uncontrolled way, the centre part 13 of the central portion 12 in a design according to the invention constitutes a planar surface of impact for the body fluid which is emitted in the region. There are no folds on the surface of impact which can transport liquid over the article in a longitudinal or transverse direction and cause leakage over the short or long sides of the article 6, 7, 8, 9.

Figure 7:
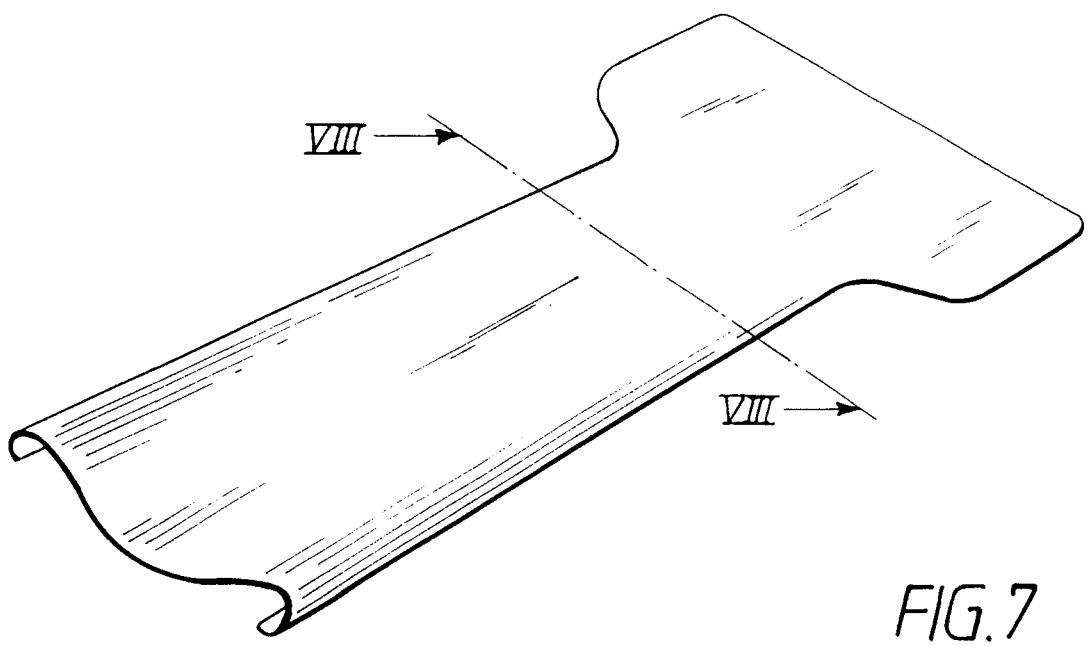
FIG. 7 shows a perspective view of a sanitary napkin according to a fifth embodiment of the invention.
Figure 8:
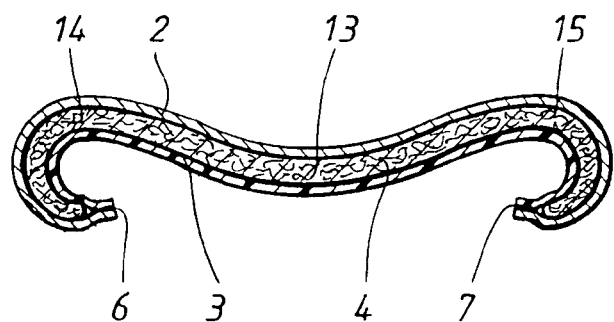
FIG. 8 shows a section along the line VIII—VIII through the sanitary napkin in FIG. 7.

An alternative embodiment of the invention, intended to create flexibility of the central portion 12, is shown in FIGS. 7–8. FIG. 7 shows the general appearance of the sanitary napkin, without any details. As earlier mentioned, an alternative to the selection of flexible materials is to design the central portion 12 with varying properties across the cross-section, so that the design in itself provides a larger flexibility. An example of such a shape of the cross-section of the central portion 12 is the M-form shown in FIG. 8. This cross-section is characterized in that the centre part 13 of the central portion bulges downwards, from the user, while the outer parts 14, 15 in relation to the centre part bulge towards the user, whereafter they curve downwards in a direction towards the backing layer 3 of the article, so that the long sides 6, 7 of the sanitary napkin point towards the backing layer 3 of the article. Such a cross-section lends a flexibility to the central portion so that it may resiliently absorb the load which arises during use, rather than, as is the case with conventional articles, being irreversibly wrinkled resulting in leakages and discomfort to the user. In the embodiment shown in FIG. 7 also the end portion 11, which is intended to be facing backwards on the user, exhibits an M-shaped cross-section. An embodiment where only the central portion 12 exhibits an M-shaped cross-section is also conceivable in accordance with the invention. Another possible embodiment of the invention is that the central portion exhibits a U-shaped cross-section, that is to say, the cross-section exhibits the same shape as above with the exception that the long sides 6, 7 do not curve inwards towards the backing layer 3 of the article.

Figure 9:
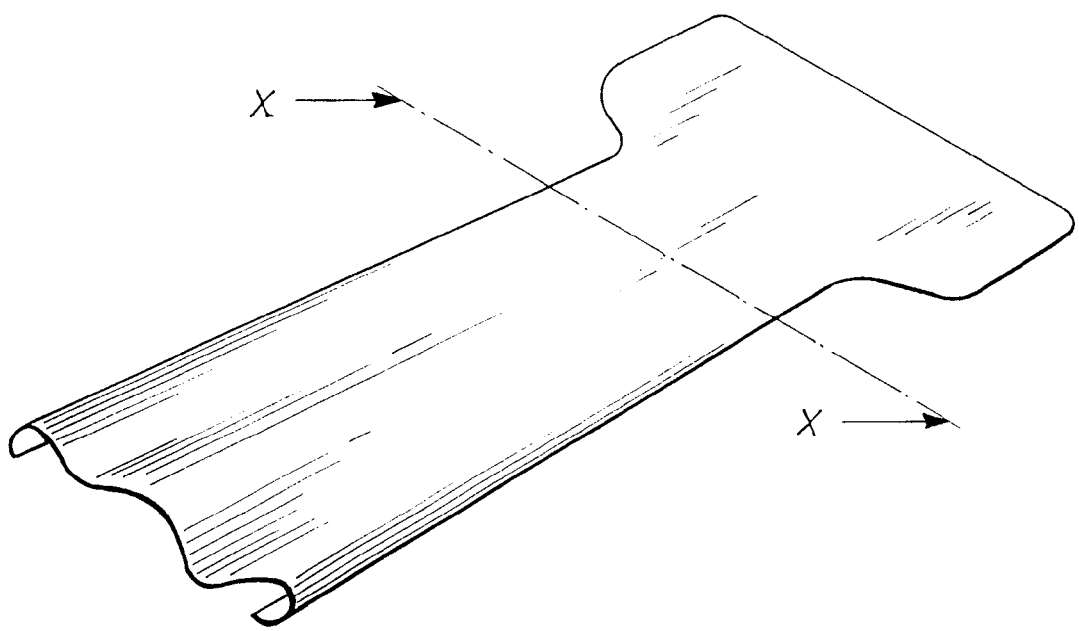
FIG. 9 shows a perspective view of a sanitary napkin according to a sixth embodiment of the invention.
Figure 10:
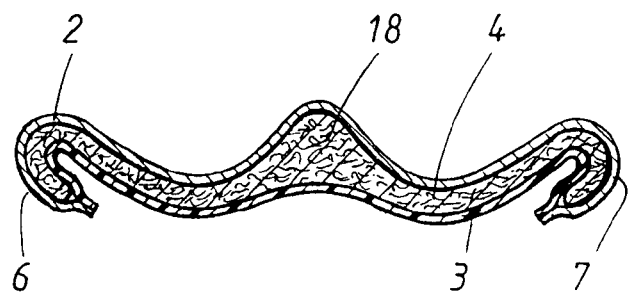
FIG. 10 shows a section along the line X—X through the sanitary napkin in FIG. 9.

An alternative design of the invention, as compared to those shown in FIGS. 7–8, is shown in FIGS. 9 and 10. FIG. 9 shows the general appearance of the sanitary napkin, without any details.

FIG. 10 shows an alternative design to the one shown in FIG. 8, of the cross-section of the central portion 12. The cross-section exhibits three ridges, as compared to the two ridges exhibited by the cross-section in FIG. 8. This implies that the sanitary napkin in FIG. 9 exhibits a central ridge, travelling between the two peripherally situated ridges, placed approximately midway between the longitudinal side edges 6, 7 of the article. The sanitary napkin in FIG. 9 exhibits a liquid-pervious layer 2, a liquid barrier layer 3 and an absorbent layer 4. Furthermore, the sanitary napkin exhibits a hump or ridge 18 arranged on the article, projecting from the liquid-pervious surface 2 and extending in the longitudinal direction of the article across the central portion 12 of the article. The intention in providing the sanitary napkin with a central ridge is to give the sanitary napkin a shape which is better adapted to the anatomy of the user. The central ridge 18, as is shown in the figure, may be built up of absorbent material, whereby it adds to the absorption capacity of the sanitary napkin. The central ridge 18 may optionally be composed of a separate shaping element, a stiff surface layer 2, or a stiff backing layer 3.

FIGS. 5, 6, 8 and 10, merely show a cross-section of the central portion 12. For reasons of clarity, the wider end portion 10 has been excluded from the figures.

For reasons of simplicity, the sanitary napkins shown in FIGS. 5, 6 and 8 are conventionally designed, with a liquid-pervious surface material, a liquid barrier backing layer, and an absorbent layer located there between. Such a design is not necessary for carrying out the invention. A design with a special shape element may equally well be used in order to provide the article with the required rigidity. The shape element may, for example, be placed between the absorbent body and the backing layer, and extend across the entire sanitary napkin or across portions thereof. Another possibility is to select a backing material, which exhibits sufficient stiffness to provide the article with rigidity.

The values which have been specified for the width of the central portion, and for the angle a between the longitudinal direction of the sanitary napkin and the main direction of the long sides of the article where the article tapers towards the central portion, may be combined freely within the scope of the invention.

The widening of the sanitary napkin from the central portion, towards one or both end portions, does not have to follow a straight line. Accordingly, it may optionally be, for example, parabolic or exponential. It may also be constituted by a straight line, broken by another straight line with a different inclination. The short sides of the article may be constituted by straight lines, but they may also exhibit other shapes such as, for example, an arc-shape.

What is claimed is:

1. An absorbent article such as a sanitary napkin, an incontinence guard or a panty-liner, which article has a generally elongate shape with a longitudinal direction and a transverse direction, said article comprising:

two long sides, two short sides, two end portions, said end portions including a front portion and a rear portion, and a central portion located between the end portions and exhibiting a transversely extending cross-sectional line from which a width of the article increases in a direction towards at least one of said short sides of the article, wherein the end portion located at said at least one of said short sides exhibits a maximum width which is larger than a width of the central portion at the cross-sectional line, wherein the long sides of the article change inclination at the cross-sectional line, the inclination being defined by an angle α between each long side of the article and a longitudinal line parallel to the longitudinal direction of the article, and wherein the width of the central portion has an upper limit of 60 mm, the angle a is 30–90°, and the article has a stiffness, at least in said front portion, which exceeds 100 N measured according to ASTM D 4032-82.

2. An absorbent article according to claim 1, further comprising a liquid-pervious layer intended to be facing a user during use, a liquid barrier layer intended to be facing away from the user during use, and an absorbent layer arranged between said liquid-pervious layer and said liquid barrier layer, and wherein a hump is arranged on the article, projecting from the liquid-pervious layer and extending in the longitudinal direction of the article at least over the central portion of the article.

3. An absorbent article according to claim 1, wherein the angle α is 35–55°.

4. An absorbent article according to claim 1, wherein the width of the central portion is between 15 mm and 60 mm.

5. An absorbent article according to claim 1, wherein the width of the central portion is between 15 mm and 45 mm.

6. An absorbent article according to claim 1, wherein the width of the central portion is between 20 mm and 35 mm.

7. An absorbent article according to claim 1, wherein the central portion exhibits a smaller width than both end portions.

8. An absorbent article according to claim 1, wherein the central portion exhibits an M-shaped cross-section.

9. An absorbent article according to claim 1, wherein the widest part of said end portion located at said at least one of said short sides is 1.5–5 times as wide as a narrowest width of the central portion.

10. An absorbent article according to claim 9, wherein the end portion located at said at least one of said short sides exhibits a width which, in a widest portion of the end portion, measures 1.5–3 times as large as a length of the end portion located at said at least one of said short sides.

11. An absorbent article according to claim 10, further comprising a liquid-pervious layer intended to be facing a user during use, and a liquid barrier layer intended to be facing away from the user during use, and wherein the article exhibits high rigidity towards bending along transversely extending bending lines at least within the front portion and the central portion, whereby said front portion and said central portion of the article exhibit high shape permanence during of said article, and said front portion of said article is inclined in relation to said central portion, in a direction towards said liquid-pervious layer, wherein said front portion forms an angle against said central portion (12).

12. An absorbent article according to claim 1, wherein angle α is defined between a longitudinal line parallel to the longitudinal direction of the article and a line passing through a point where the front portion of said absorbent article begins to widen.

13. An absorbent article according to claim 1, wherein the width of the article increases in a direction towards only one of said short sides of the article, so as to define said angle α at only one end portion.

* * * * *